(12) United States Patent
Potter et al.

(10) Patent No.: US 9,015,191 B2
(45) Date of Patent: *Apr. 21, 2015

(54) METHODS AND APPARATUS TO ENHANCE QUERIES IN AN AFFINITY DOMAIN

(71) Applicant: General Electric Company, Schenectady, NY (US)

(72) Inventors: Matthew G. Potter, Beaverton, OR (US); Guy Vesto, Kildeer, IL (US); John Baartz, Tower Lakes, IL (US); Paul Isabelli, Lake Villa, IL (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/015,395

(22) Filed: Aug. 30, 2013

(65) Prior Publication Data

US 2013/0346448 A1 Dec. 26, 2013

Related U.S. Application Data

(63) Continuation of application No. 12/788,038, filed on May 26, 2010, now Pat. No. 8,549,030.

(51) Int. Cl.
*G06F 17/30* (2006.01)
*G06F 19/00* (2011.01)

(52) U.S. Cl.
CPC ........ *G06F 17/30011* (2013.01); *G06F 19/321* (2013.01); *G06F 19/322* (2013.01)

(58) Field of Classification Search
CPC ............... G06F 17/30427; G06F 17/30569; G06F 19/321; G06F 19/322
USPC .......................................................... 707/769
See application file for complete search history.

(56) References Cited

U.S. PATENT DOCUMENTS

| | | |
|---|---|---|
| 2004/0243614 A1 | 12/2004 | Boone et al. |
| 2007/0118540 A1 | 5/2007 | Guo |
| 2008/0071825 A1 | 3/2008 | Guo |
| 2009/0222406 A1 | 9/2009 | Allred et al. |
| 2011/0196886 A1 | 8/2011 | Ho et al. |

OTHER PUBLICATIONS

The United States Patent and Trademark Office, "Non-Final Office action," issued in connection with U.S. Appl. No. 12/788,038 on Apr. 10, 2012 (11 pages).
The United States Patent and Trademark Office, "Final Office action," issued in connection with U.S. Appl. No. 12/788,038 on Aug. 22, 2012 (12 pages).
The United States Patent and Trademark Office, "Notice of Allowance," issued in connection with U.S. Appl. No. 12/788,038 on Aug. 21, 2013 (14 pages).

*Primary Examiner* — Jorge A Casanova

(57) ABSTRACT

Methods and apparatus to enhance queries in an affinity domain are disclosed herein. An example method of providing a query service in an affinity domain includes receiving a query including one or more template identifiers that indicate conformance with a standard related to content of a document; generating an expression including the one or more template identifiers to define a search of a registry; performing the search of the registry according to the expression, wherein the search is configured to identify documents including the one or more template identifiers; and conveying the identified documents to an entity associated with the query.

20 Claims, 5 Drawing Sheets

… (1)

METHODS AND APPARATUS TO ENHANCE QUERIES IN AN AFFINITY DOMAIN

RELATED APPLICATION

This patent arises from a continuation of U.S. patent application Ser. No. 12/788,038, filed on May 26, 2010, now U.S. Pat. No. 8,549,030, which is hereby incorporated herein by reference in its entirety.

FIELD OF THE DISCLOSURE

The present disclosure relates generally to healthcare information systems and, more particularly, to methods and apparatus to enhance queries in an affinity domain.

BACKGROUND

Healthcare environments, such as hospitals and clinics, typically include information systems (e.g., electronic medical record (EMR) systems, lab information systems, outpatient and inpatient systems, hospital information systems (HIS), radiology information systems (RIS), storage systems, picture archiving and communication systems (PACS), etc.) to manage information such as, for example, patient medical histories, imaging data, test results, diagnosis information, management information, financial information, and/or scheduling information.

Healthcare practitioners, patients, researchers, etc. may desire access to patient information or other information at various points in a healthcare workflow. For example, during and/or after surgery, medical personnel may access patient information, such as images of an anatomy of a patient, stored in a medical information system. In another example, researchers may desire groups of medical records of one or more particular types for analysis and study.

SUMMARY

An example method of providing a query service in an affinity domain includes receiving a query including one or more template identifiers that indicate conformance with a standard related to content of a document. Further, the example method includes generating an expression including the one or more template identifiers to define a search of a registry. Further, the example method includes performing the search of the registry according to the expression, wherein the search is configured to identify documents including the one or more template identifiers. Further, the example method includes conveying the identified documents to an entity associated with the query.

An example tangible machine readable medium has instructions stored thereon that, when executed, cause a machine to receive a query including one or more template identifiers that indicate conformance with a standard related to content of a document. Further, the example tangible machine readable medium has instructions stored thereon that, when executed, cause a machine to generate an expression including the one or more template identifiers to define a search of a registry. Further, the example tangible machine readable medium has instructions stored thereon that, when executed, cause a machine to perform the search of the registry according to the expression, wherein the search is configured to identify documents including the one or more template identifiers. Further, the example tangible machine readable medium has instructions stored thereon that, when executed, cause a machine to convey the identified documents to an entity associated with the query.

An example apparatus to provide a query service in an affinity domain includes a communication interface to receive a query including one or more template identifiers that indicate conformance with a standard related to content of a document. Further, the example apparatus includes a first one of a plurality of query modules, the first query module being associated with the standard associated with the one or more template identifiers. The example first query module includes a parameter mechanism to generate an expression including the one or more template identifiers to define a search of a registry. Further, the example first query module includes a content matcher to perform the search of the registry according to the expression, wherein the search is configured to identify documents including the one or more template identifiers. Further, the communication interface of the example apparatus is to convey the identified documents to an entity associated with the query.

Figure 1:
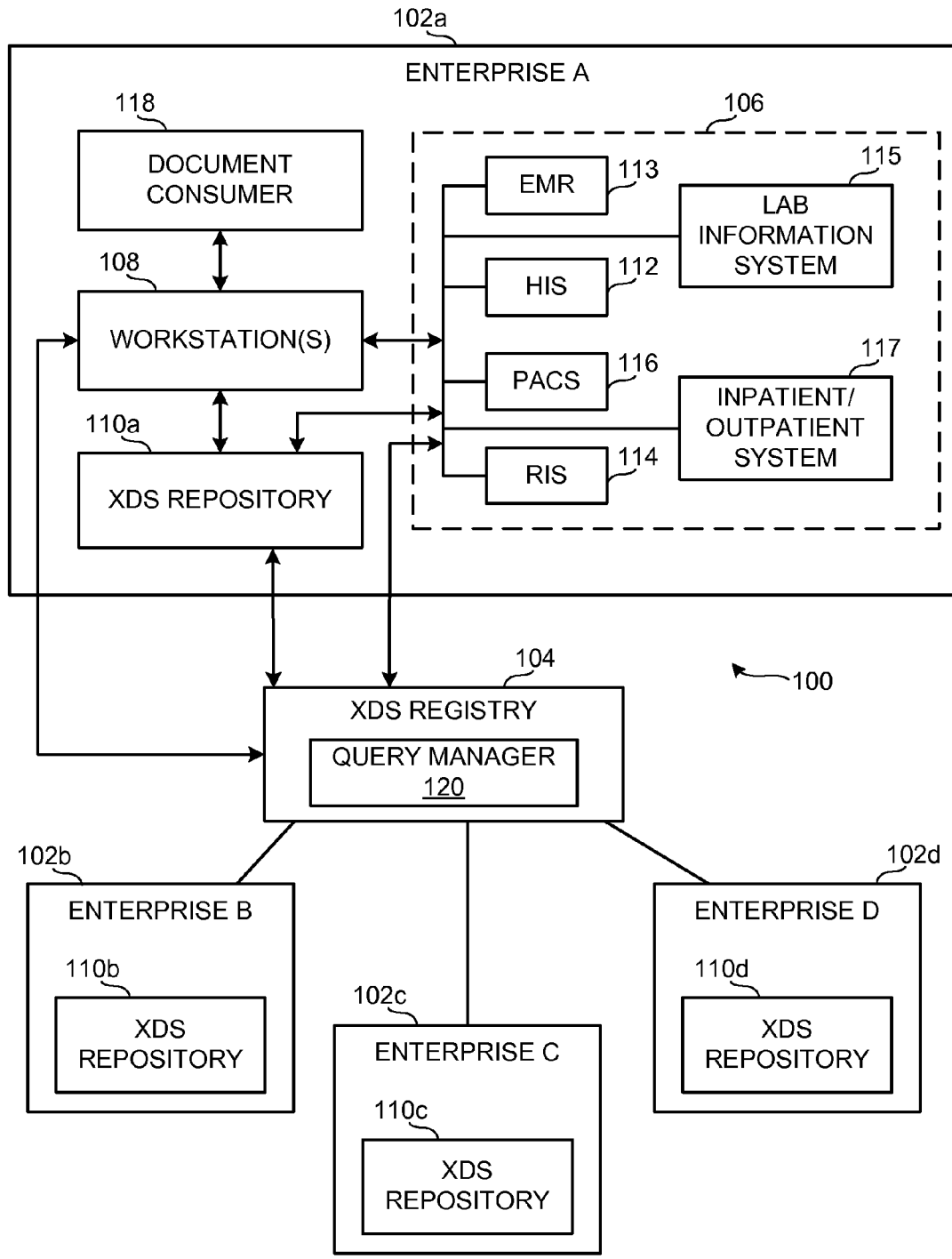
FIG. 1 is a block diagram of an example healthcare information system.

The foregoing summary, as well as the following detailed description of certain implementations of the methods, apparatus, systems, and/or articles of manufacture described herein, will be better understood when read in conjunction with the appended drawings. It should be understood, however, that the methods, apparatus, systems, and/or articles of manufacture described herein are not limited to the arrangements and instrumentality shown in the attached drawings.

DETAILED DESCRIPTION

Although the following discloses example methods, apparatus, systems, and articles of manufacture including, among other components, firmware and/or software executed on hardware, it should be noted that such methods, apparatus, systems, and/or articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

A variety of clinical data and healthcare information is available throughout various clinical, medical and other types of data systems. Healthcare practitioners (e.g., physicians, surgeons, technicians, nurses, administrative support staff, etc.) spend a significant amount of time analyzing various types of healthcare information including, for example, radiology images, ultrasound images, magnetic resonance imaging (MRI) scans, etc. The purpose of an analysis may range from diagnosing a condition, assessing a recovery process, identifying abnormalities, and/or otherwise caring for a patient. Researchers and/or other types of users may also access healthcare information systems for purposes of gathering clinical and/or other types of data for research, statistical analysis, and/or other purposes.

To enable practitioners, patients, researchers, etc. (which are sometimes referred to herein as document consumers) gathering and/or accessing data, medical data systems typically present document consumers with one or more query options. Document consumers typically enter information into and/or make selections from a user interface, which facilitates communication between the document consumers and, for example, a database storing information (e.g., medical images, test results, financial data or records, etc.). In response to such queries, a healthcare data system performs one or more searches of the records stored therein and presents search results to the querying document consumer.

The example methods, apparatus, systems, and/or articles of manufactures described herein improve the ability of a document consumer to query sources of healthcare data. The example methods, apparatus, systems, and/or articles of manufacture described herein provide one or more filtering mechanisms that enable a querying document consumer to more efficiently and accurately identify and/or retrieve desired information (e.g., one or more healthcare documents). In particular, the example methods, apparatus, systems, and/or articles of manufacture enhance query results by filtering semantically structured sections in structured and semi-structured documents. Further, the example methods, apparatus, systems, and/or articles of manufacture described herein improve performance levels of one or more components of a healthcare information system that facilitate, for example, a query interface, a search of content source(s), presentation of search results, and other components involved in a query service. Further, the example methods, apparatus, systems, and/or articles of manufacture described herein reduce computational and bandwidth overhead for devices being used by a document consumer, as the example filtering mechanisms described herein provide more accurate search results. Additional examples, aspects, and advantages of the example methods, apparatus, systems, and/or articles of manufacture are described in greater detail below in connection with an example healthcare data system.

As described in greater detail below, the example methods, apparatus, systems, and/or articles of manufacture described herein enable document consumers to query a healthcare data system using one or more filtering mechanisms configured to identify documents containing specified template information. In some examples, the document consumer specifies one or more template identifiers to be used by the filtering mechanism(s) to limit or filter search results according to the specified template identifier(s). Additionally or alternatively, in some examples, the document consumer specifies one or more lists of template identifiers to be used by the filtering mechanism(s) to limit or filter search results according to the specified list(s) of template identifiers.

A template identifier used by the example filtering mechanism(s) described herein is associated with a document (e.g., a healthcare record) and defined using any suitable code (e.g., in a descriptor field or header). The template identifier associated with a document is an indication of the document's conformance with a certain standardized format and/or a set of standardized rules. In other words, the template identifier associated with a document includes information regarding whether or not the content of the document conforms to a certain standard and, if so, to which aspect or portion of the standard the document conforms.

For example, the Health Level 7 (HL7) Clinical Document Architecture (CDA) includes a plurality of template identifiers corresponding to the plurality of document formats conforming to CDA rules and constraints. For example, a first template identifier can indicate that the corresponding document conforms to the HL7 Continuity of Care standard for clinical documents. Knowing that the document conforms to such a standard as indicated by the template identifier informs the document consumer and/or a device or system receiving the template identifier that the document contains certain content and/or types of content. To continue the above example, when the template identifier indicates that the document conforms to the HL7 Continuity of Care standard, the document consumer and/or a device receiving the template identifier knows that the document includes certain sections regarding patient problems, medications, allergies, immunizations, laboratory results, etc.

A second example CDA template identifier indicates that a CDA header associated with the document conforms to certain rules regarding the inclusion of contact information for people and/or organizations referenced in the document. A third example CDA template identifier indicates that the document is a medical summary that conforms to certain rules regarding medical summaries such as, for example, the inclusion of a list of problems, medications, and allergies for a patient associated with the document. The example methods, apparatus, systems, and/or articles of manufacture described herein can utilize additional or alternative template identifiers associated with additional or alternative standards, as the above examples are provided for purposes of illustration and not limitation.

The example methods, apparatus, systems, and/or articles of manufacture described herein may be utilized in, for example, an affinity domain including a plurality of healthcare data systems and/or data sources associated with domain members. An affinity domain may refer to a group of member enterprises that have agreed to facilitate a sharing of data among members. For example, the example filtering mechanisms described herein may be utilized in the Integrated Healthcare Enterprise (IHE) Cross-Enterprise Document Sharing (XDS) Integration Profile. In particular, the example filtering mechanisms described herein can be implemented in association with a document registry of an XDS affinity domain. As described in greater detail below, the document registry, which enables querying of document repositories, can use the example filtering mechanisms described herein to enhance a document consumer's ability to efficiently query the data sources of the affinity domain in which the registry is implemented. The example methods, apparatus, systems, and/or articles of manufacture described herein can be implemented in additional or alternative healthcare data systems, as the XDS system described below is provided for purposes of illustration and not limitation.

FIG. 1 is a block diagram of an example healthcare data system 100 capable of implementing the example methods, apparatus, systems, and/or articles of manufacture described herein to enhance queries in an affinity domain. The example healthcare data system 100 of FIG. 1 includes a plurality of healthcare enterprises 102*a-d* that are members of an affinity domain. In the illustrated example of FIG. 1, the enterprise labeled with reference numeral 102*a* is illustrated and described herein as a hospital. However, any of the enterprises 102a-d may be any type of healthcare facility such as, for example, a clinic, a physician's office, a laboratory, a testing center, etc. Further, while FIG. 1 illustrates the components of the hospital 102a, the other enterprises (enterprises 102b-d) may include additional, alternative, and/or similar components, although not shown in FIG. 1 for purposes of brevity and not limitation.

The example healthcare data system 100 of FIG. 1 implements an IHE XDS integration profile to facilitate the sharing (e.g., registration, distribution, access, etc.) of healthcare data among the healthcare enterprises 102a-d (referred to as an Affinity Domain in IHE XDS terminology) via a common registry 104. The XDS profile includes a common set of standards or policies for the healthcare enterprises 102a-d, which agree to share medical data using a common infrastructure. While the example healthcare data system 100 of FIG. 1 is shown as implemented by a XDS integration profile, any additional or alternative medical data sharing system (e.g., any health information exchanges (HIEs) and/or regional health information organizations (RHIOs) designed to enable a plurality of healthcare enterprises to exchange healthcare information) can be used to implement the example methods, apparatus, systems, and/or articles of manufacture described herein. Moreover, the example methods, apparatus, systems, and/or articles of manufacture described herein may be implemented on a healthcare data system 100 without information sharing capabilities, such as a standalone physician office or clinic.

The example hospital 102a includes a healthcare information system 106, one or more workstations 108, and a repository 110a. The healthcare information system 106 includes one or more of a hospital information system (HIS) 112, an electronic medical record system (EMR) 113, a radiology information system (RIS) 114, a lab information system 115, a picture archiving and communication system (PACS) 116, and an inpatient/outpatient system 117. In the illustrated example, the hospital information system 112, the electronic medical record system 113, the radiology information system 114, the lab information system 115, the PACS 116, and the inpatient/outpatient system 117 are housed in the hospital 102a and locally archived. However, in other implementations, one or more elements of the example healthcare information system 106 may be housed one or more other suitable locations. Furthermore, one or more components of the medical information system 106 may be combined and/or implemented together. For example, the radiology information system 114 and/or the PACS 116 may be integrated with the hospital information system 112; the PACS 116 may be integrated with the radiology information system 114; and/or the six example information systems 112, 113, 114, 115, 116, and/or 117 may be integrated together. Preferably, information (e.g., test results, observations, diagnosis, discharges, admissions, findings, reports, etc.) is entered into the elements of the example healthcare information 106 by healthcare practitioners (e.g., radiologists, physicians, technicians, administrators, etc.) before, after, and/or during a patient examination and/or testing session. In some examples, the equipment (e.g., an MRI machine) of these systems (e.g., the PACS 116) stores the information (e.g., an MRI scanned image) automatically upon acquiring the information.

The hospital information system 112 stores healthcare information such as clinical reports, patient information, practitioner information, and/or financial data received from, for example, personnel at a hospital, clinic, and/or a physician's office. The EMR system 113 stores information related to patients and/or practitioners, medical histories, current treatment records, etc. The radiology information system 114 stores information such as, for example, radiology reports, x-ray images, messages, warnings, alerts, patient scheduling information, patient demographic data, patient tracking information, and/or physician and patient status monitors. Additionally, the radiology information system 114 enables exam order entry (e.g., ordering an x-ray of a patient) and image and film tracking (e.g., tracking identities of one or more people that have checked out a film).

The lab information system 115 stores clinical information such as lab results, test scheduling information, corresponding practitioner(s), and/or other information related to the operation(s) of one or more labs at the corresponding healthcare facility. The PACS 116 stores medical images (e.g., x-rays, scans, three-dimensional renderings, etc.) as, for example, digital images in a database or registry. Images are stored in the PACS 116 by healthcare practitioners (e.g., imaging technicians, physicians, radiologists) after a medical imaging of a patient and/or are automatically transmitted from medical imaging devices to the PACS 116 for storage. In some examples, the PACS 116 may also include a display device and/or viewing workstation to enable a healthcare practitioner to communicate with the PACS 116. The inpatient/outpatient system 117 stores information related to the admission and discharge of patients such as follow up schedules, patient instructions provided by a practitioner, prescription information, presenting symptoms, contact information, etc.

While example types of information are described above as being stored in certain elements of the healthcare information system 106, different types of healthcare data may be stored in one or more of the hospital information system 112, the EMR system 113, the radiology information system 114, the lab information system 115, the PACS 116, and/or the inpatient/outpatient system 117. Further, the information stored in these elements may overlap and/or share types of data.

The hospital information system 112, the EMR system 113, the radiology information system 114, the lab information system 115, the PACS 116, and/or the inpatient/outpatient system 117 may be in communication via, for example, a Wide Area Network (WAN) such as a private network or the Internet. More generally, any of the coupling(s) described herein, such as the coupling(s) between the registry 104 and any of the enterprises 102a-d, may be via a network. In such instances, the network may be implemented by, for example, the Internet, an intranet, a virtual private network, a wired or wireless Local Area Network, and/or a wired or wireless Wide Area Network. In some examples, the healthcare information system 106 also includes a broker (e.g., a Mitra Imaging's PACS Broker) to allow medical information and medical images to be transmitted together and stored together.

In some examples, information stored in one or more components of the medical information system 106 is formatted according to the HL7 clinical communication protocol, the Digital Imaging and Communications in Medicine (DICOM) protocol, and/or any other suitable standard and/or protocol. The equipment used to obtain, generate, and/or store the information of the medical information system 106 may operate in accordance with the HL7 clinical communication protocol, the DICOM protocol, and/or any other suitable standard and/or protocol.

The repository 110a, which is shown as an XDS repository in the example of FIG. 1, facilitates the sharing of healthcare documents generated by the medical information system 106 with other enterprises (e.g., enterprises 102b-d). In particular, the repository 110a receives images, medical reports, administrative information, financial data, insurance information, and/or other healthcare information from the healthcare information system 106 and stores such information in, for example, a database or any suitable data structure. Thus, to use XDS terminology, the medical information 106 is a document source that provides the repository 110a clinical data to be shared among the enterprises 102a-d. As shown in the example of FIG. 1, each of the enterprises 102b-d includes an XDS repository 110b-d that functions in a similar manner as the repository 110a of the hospital 102a. Thus, the XDS repositories 110a-d collectively store healthcare documents and the content thereof that are capable of being shared across the affinity domain of the example healthcare data system 100 of FIG. 1.

Further, the repository 110a receives metadata associated with the images, medical reports, administrative information, financial data, insurance information, and/or other healthcare information from the medical information system 106 and forwards the metadata to the registry 104, which stores the metadata in a database and/or any other suitable storage mechanism. The metadata is used by the registry 104 to index the healthcare information stored at the repository 110a (along with the information stored at the repositories of the other enterprises 102b-d). The metadata corresponds to one of more types of identifying information (e.g., identification numbers, patient names, record numbers, social security numbers, payment status indicators, or any other identifying) associated with, for example, medical reports stored at the repositories 110a-d. The registry 104 is capable of receiving queries into the contents of the repositories 110a-d of the healthcare data system 100 and using the indexed metadata to satisfy the queries.

In the illustrated example, the registry 104 receives such queries from a document consumer 118. The document consumer 118 may be associated with one or more of the enterprises 120a-d and/or may have access to the registry 104 via alternative(s) associations. For example, the document consumers 118 may be a researcher that was granted access to the contents of the repositories 110a-d of the affinity domain defined by the example healthcare data system 100. In the example of FIG. 1, the document consumer 118 uses a first one of the workstation(s) 108 to query the registry 104. The workstation(s) 108 may access the registry 104 via the repository 110a or directly, as illustrated in FIG. 1.

The workstation(s) 108 may be any equipment (e.g., a personal computer) capable of executing software that permits electronic data (e.g., medical reports) and/or electronic medical images (e.g., x-rays, ultrasounds, MRI scans, clinical reports, test results, etc.) to be acquired, stored, or transmitted for viewing and operation. The workstation(s) 108 receive commands and/or other input from a user (e.g., a physician, surgeon, nurse, or any other healthcare practitioner) via, for example, a keyboard, mouse, track ball, microphone, etc. The workstation(s) include and/or are coupled to one or more presentation devices (e.g., a standard computer monitor, speakers, touch-screen devices, specialized monitors to view specific images such as x-rays, magnetic resonance imaging (MRI) scans, etc.) capable of presenting images, video, audio, text, etc. to one or more practitioners, such as the document consumer 118.

Multiple workstations 108 can communicate with each other, the healthcare information system 106, and/or the XDS repository 110a and registry 104 to obtain shared medical information and convey the same to the user of the workstation(s) 108. Further, the workstation(s) 108 are capable of implementing a user interface to enable a healthcare practitioner to interact with the healthcare data system 100 and/or the registry 104 and the components thereof. In the illustrated example, the user interface enables a search of one or more components or elements of the healthcare data system 100 and/or one or more external databases containing relevant healthcare information. The document consumer 118 can use such an interface to query medical resources using different criteria such as, for example, a patient name, a patient identification number, a social security number, date(s) of treatment(s), type(s) of treatment, etc.

Using the example methods, apparatus, systems, and/or articles of manufacture disclosed herein, the document consumer 118 can also query medical resources (e.g., the repositories 110a-d) using criteria related to one or more template identifiers. The document consumer 118 can specify, via the user interface implemented by the workstation 108, one or more template identifiers to be used as search criteria by the registry 104. The user interface may provide a list of available template identifiers from which the document consumer 118 may make one or more selections, a text entry box to receive one or more template identifiers as text, and/or any other suitable options for the document consumer 118 to specify which template identifier(s) are to be included in the search criteria.

As described above, template identifiers indicate to the document consumer 118 and/or a device receiving the template identifiers what type of content is included in the corresponding healthcare document. Thus, the examples described herein expand the catalog of metadata that the registry 104 exposes to the document consumer 118 to include template identifiers of one or more standards. In the illustrated example of FIG. 1, the template identifiers used as metadata by the registry 104 are CDA identifiers. However, additional or alternative standards that include template identifiers may be used by a query mechanism implementing the examples described herein.

To provide the enhanced querying described herein, the registry 104 of the example healthcare data system 100 of FIG. 1 includes a query manager 120. The example query manager 120 can be implemented in additional or alternative elements and/or locations in the example healthcare data system 100 of FIG. 1 and/or any other type of medical data system. For example, the query manager 120 may be implemented in one or more of the XDS repositories 110a-d, the workstation(s) 108, and/or one or more elements of the medical information system 106 (e.g., the hospital information system 112, the electronic medical record system 113, the radiology information system 114, the lab information system 115, the PACS 116, and/or the inpatient/outpatient system 117). As described in greater below in connection with FIG. 2, the example query manager 120 of FIG. 1 provides, for example, the document consumer 118 with enhanced query abilities by utilizing one or more filtering mechanisms. Generally, the example filtering mechanisms described herein ensure that the document consumer 118 receives search results that include documents having desired content and/or types of desired content. The example query manager 120 provides additional or alternative features, benefits, and/or improvements as described below.

Figure 2:
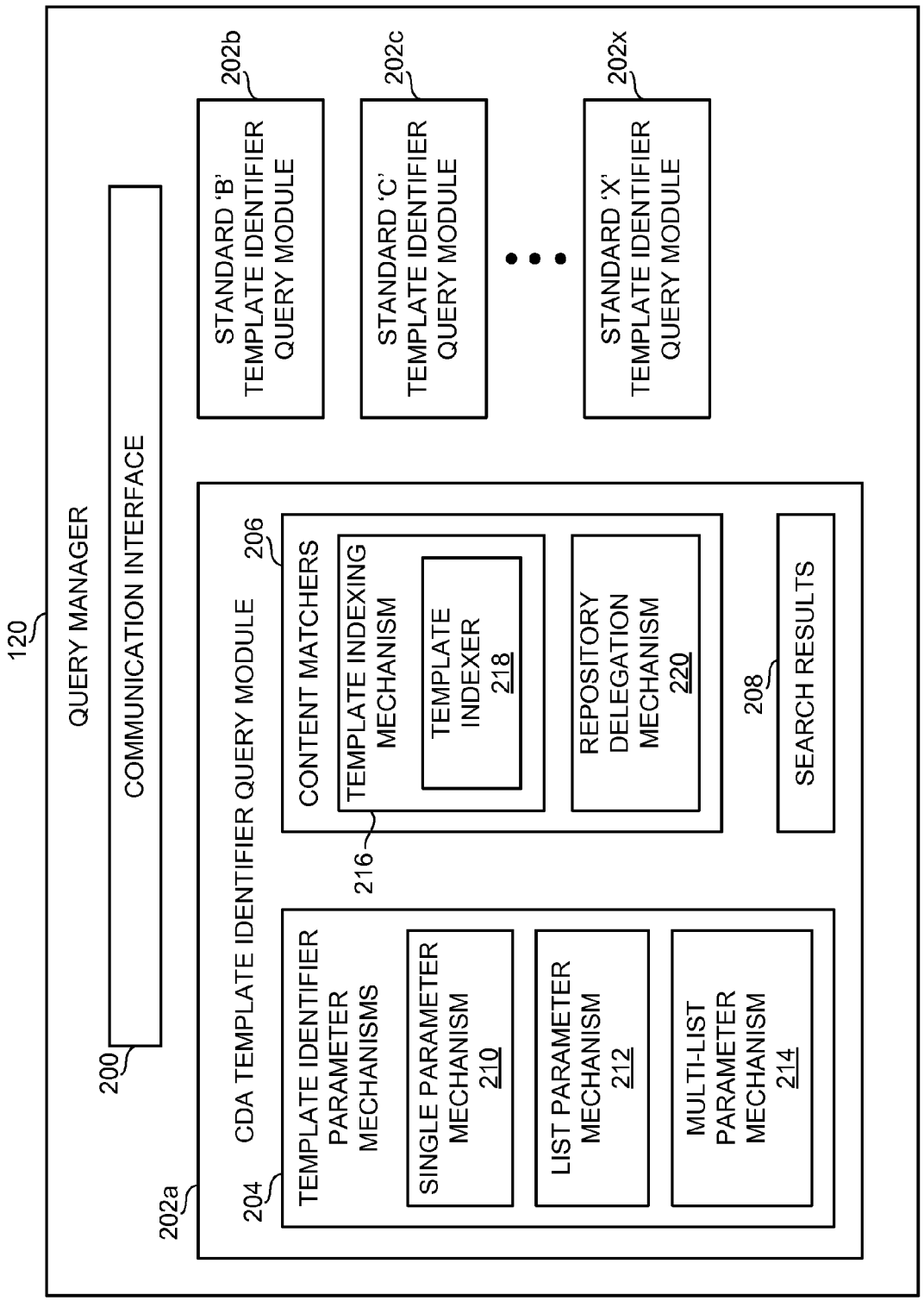
FIG. 2 is a block diagram of an example apparatus that may be used to implement the example query module of FIG. 1.

FIG. 2 is a block diagram of an example apparatus that may be used to implement the example query manager 120 of FIG. 1. In the illustrated example of FIG. 2, the example query manager 120 includes a communication interface 200. The example communication interface 200 conveys and receives data, instructions, and/or any other suitable information to and from one or more of the elements of the healthcare data system 100, such as the workstation(s) 108 being used by the document consumer 118. For example, the communication interface 200 may receive a query including a template identifier(s) from the document consumer 118 via one of the workstation(s) 108 and/or any other suitable device (e.g., a personal computer having software and/or programming to enable access of the XDS registry 104) usable by the document consumer 118.

To handle such a query, the example query manager 120 includes a plurality of template identifier query modules 202a-x, each of which corresponds to a certain standard. That is, the example query manager 120 is capable of receiving and using different types of template identifiers corresponding to different standards and/or standardization sets of rules. For purposes of illustration and not limitation, FIG. 2 illustrates a first one of the template identifier query modules 202a that corresponds to the CDA standard. However, the example query manager 120 described herein can utilize template identifiers of any of a plurality of standards using the other template identifier query modules 202b-x.

The example CDA template identifier query module 202a includes a plurality of template identifier parameter mechanisms 204 and a plurality of content matchers 206. In general, a selected one of the parameter mechanisms 204 defines a search to be performed by a selected one of the content matchers 206 that generates search results 208. To define the search, the selected one of the parameter mechanisms 204 generates a logical expression or statement including the template identifier(s) received with the query request. The logical expression or statement reflects a search interaction (or type of search) between the received template identifier(s) that was indicated by, for example, the document consumer 118 using a user interface of the workstation(s) 108 (e.g., by selecting one or more corresponding options from a drop-down list, by selecting one or more checkmark boxes, etc.).

In the illustrated example of FIG. 2, a single parameter mechanism 210 generates a logical expression that causes the selected one of the content matchers 206 to search for documents including the single received template identifier. That is, the received template identifier is the sole template identifier parameter used in the search performed by the selected content matcher 206. As a result, the search results 208 associated with the received query will include document(s) known to the registry 104 having metadata indicating that the identified document(s) include one or more instances of the received template identifier and, thus, include content defined by the received template identifier (e.g., an active medication list, a list of current allergies, etc.).

In the illustrated example of FIG. 2, a list parameter mechanism 212 generates a logical expression that causes the selected one of the content matchers 206 to search for documents including any (e.g., using a logical 'OR' operator) or each (e.g., using a logical 'AND' operator) of a plurality of template identifiers included in a received list. Whether to define the search interaction as an 'OR' operation or an 'AND' operation may be indicated in a selection associated with the received list of template identifiers. As a result, when the list parameter mechanism 212 is to define the search interaction as an 'OR' operation, the search results 208 associated with the received list of template identifiers will include document(s) known to the registry 104 having metadata indicating that the identified document(s) includes one or more instances of any of the template identifiers of the list. Further, when the list parameter mechanism 212 is to define the search interaction as an 'AND' operation, the search results 208 associated with the received list of template identifiers will include document(s) known to the registry 104 having metadata indicating that the identified document(s) includes one or more instances of each of the template identifiers of the list.

In the illustrated example, the multi-list parameter mechanism 214 generates a logical expression that causes the selected one of the content matchers 206 to search for documents including any of a first list of template identifiers and any of a second list of template identifiers. Thus, the logical expression generated by the multi-list parameter mechanism 214 includes a first portion involving an 'OR' operator applied to the first list of template identifiers; a second portion involving an 'OR' operator applied to the second list of template identifiers; and a third portion involving an 'AND' operation applied to the results of the first and second portions.

Moreover, the example multi-list parameter mechanism 214 is capable of generating a logical expression or statement for more than two lists of template identifiers. For example, when first, second, and third lists of template identifiers are received by the communication interface 200 with an instruction to use the multi-list parameter mechanism 214, the logical expression generated by the multi-list parameter mechanism 214 includes a first portion involving an 'OR' operator applied to the first list of template identifiers; a second portion involving an 'OR' operator applied to the second list of template identifiers; a third portion involving an 'OR' operator applied to the third list; and a fourth portion involving an 'AND' operation applied to the results of the first, second, and third portions. As a result, the search results 208 associated with the received lists of template identifiers will include document(s) known to the registry 104 having metadata indicating that the identified document(s) includes any of the template identifiers specified in each of the received lists of template identifiers.

Additional or alternative parameter mechanisms to define additional or alternative search interactions between received template identifier(s) or lists of template identifiers can be implemented by the example CDA template identifier query module 202a and/or, more generally, the example query manager 120 of FIGS. 1 and/or 2.

A selected one of the content matchers 206 uses the logical expression or statement generated by the selected one of the parameter mechanisms 204 to perform a search of, for example, the metadata stored in the registry 104. As described above, the registry 104 stores metadata corresponding to the data stored in the repositories 110a-d of the example healthcare data system 100 of FIG. 1. In the illustrated example, the metadata of the registry 104 includes information regarding which template identifiers are associated with each of the documents stored in the repositories 110a-d. The example content matchers 206 use such metadata and the logical expression received from the parameter mechanisms 204 (which includes the template identifier(s) received at the communication interface 200) to identify matching documents.

The example content matchers 216 of FIG. 2 include a template indexing mechanism 216. In general, the example template indexing mechanism 216 creates an index of CDA documents and searches for matches between the template identifier(s) of the received logical expression and the data of the index. Of course, the example template indexing mechanism also adheres to the logical interaction(s) between the template identifiers as defined in the logical expression or statement generated by the parameter mechanisms 204, as described above.

To generate the index of template identifier information, the example template indexing mechanism 216 includes a template indexer 218, which may store the index described herein. As described above, the example repositories 110a-d of FIG. 1 convey metadata associated with received healthcare documents to the registry 104. In the illustrated example of FIG. 2, when the communication interface 200 receives metadata and/or other type(s) of identifying data indicating the corresponding healthcare document is a registered CDA document, the metadata and/or other identifying data is conveyed to the template indexer 218 (e.g., in addition to conveying the metadata to one or more additional or alternative components of the example query manager 120). The example template indexer 218 determines whether the CDA document includes any template identifiers and, if so, adds the metadata corresponding to the CDA document and indication(s) of the included template identifier(s) to the index. In other words, the example template indexer 218 indexes CDA documents received at the registry 104 with respect to the template identifier(s) found within or associated with the received CDA document. The example template indexer 218 is described in greater detail below in connection with FIG. 4.

In response to receiving a query (e.g., one or more template identifiers and a corresponding logical statement defined the specified search interaction therebetween generated by the selected one of the parameter mechanisms 204), the example template indexing mechanism 216 uses the index generated and maintained by the template indexer 218 to search the registry 104 for metadata matching the received template identifiers and/or metadata associated with the received template identifiers. The example template indexer 218 can use any suitable search algorithm to parse through the indexed metadata and to identify any template identifier metadata matching the template identifiers received in the query according to the logical statement or expression generated by the selected one of the parameter mechanisms 204. When such matching metadata is identified, the example template indexing mechanism 216 of FIG. 2 assigns the matching metadata as the search results 208. In the illustrated example, the search results 208 are accessible by the communication interface 200, which conveys the search results 208 to, for example, a component of the registry 104 capable of retrieving the corresponding document from one or more of the repositories 110a-d. The registry 104 may convey the retrieved document(s) to the workstation(s) 108 being used by the querying document consumer 118 and/or any suitable device (e.g., a device designated to receive the results in the query request and/or in one or more secondary instructions designating a destination device) using any suitable method (e.g., electronic mail, facsimile, mail, display information to be presented on the workstation(s) 108, etc.). The search results can include a list of matching documents including links to matching documents and/or copies of the matching documents.

In addition to the example template indexing mechanism 216, the example content matchers 206 of FIG. 2 include a repository delegation mechanism 220. The example repository delegation mechanism 220 of FIG. 2 works in conjunction with one or more application programming interfaces (APIs) implemented at the one or more repositories 110a-d. That is, in the illustrated example, the repositories 110a-d include components or programs that, in addition to supporting standard XDS transactions, also provide one or more APIs to enable searches using, for example, CDA template identifiers.

When the repository delegation mechanism 220 receives a query including one or more template identifiers, the example repository delegation mechanism 220 parses through the metadata of the registry 104 to identify any matching metadata related to the received template identifier(s). When matching metadata is identified in the search, the example repository delegations mechanism 220 calls one or more of the APIs implemented in one of the repositories 110a-d. This function call can be via the communication interface 200 using the search results 208 as parameters in the function call. The APIs implemented in the repositories 110a-d are capable of filtering the search results, for example, in a manner similar to the parameter mechanisms 204 of the query manager 120. Therefore, the filtering aspects of the query are satisfied by the APIs of the repositories 110a-d.

In addition to the template identifier query modules 202a-x described herein, the example query manager 120 includes other query module(s) to handle additional aspects of a query (e.g., a keyword, a specified date, a patient name, etc.). In some examples, the additional aspects of the query are conveyed to the content matchers 206, which may include components to handle searching of the registry 104 using the additional aspects.

While an example manner of implementing the query manager 120 of FIG. 1 has been illustrated in FIG. 2, one or more of the elements, processes and/or devices illustrated in FIG. 2 may be combined, divided, re-arranged, omitted, eliminated and/or implemented in any other way. Further, the example communication interface 200, the example query modules 202a-x, the example template identifier parameter mechanisms 204 including the example single parameter mechanism 210, the example list parameter mechanism 212, and the multi-list parameter mechanism 214, and the example content matchers 206 including the template indexing mechanism 216 and the repository delegation mechanism 220, and/or, more generally, the example query manager 120 of FIG. 2 may be implemented by hardware, software, firmware and/or any combination of hardware, software and/or firmware. Thus, for example, any of the example communication interface 200, the example query modules 202a-x, the example template identifier parameter mechanisms 204 including the example single parameter mechanism 210, the example list parameter mechanism 212, and the multi-list parameter mechanism 214, and the example content matchers 206 including the template indexing mechanism 216 and the repository delegation mechanism 220, and/or, more generally, the example query manager 120 of FIG. 2 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the example communication interface 200, the example query modules 202a-x, the example template identifier parameter mechanisms 204 including the example single parameter mechanism 210, the example list parameter mechanism 212, and the multi-list parameter mechanism 214, and the example content matchers 206 including the template indexing mechanism 216 and the repository delegation mechanism 220, and/or, more generally, the example query manager 120 of FIG. 2 are hereby expressly defined to include a tangible medium such as a memory, DVD, CD, etc., storing the software and/or firmware. Further still, the example query manager 120 of FIG. 2 may include one or more elements, processes and/or devices in addition to, or instead of, those illustrated in FIG. 2, and/or may include more than one of any or all of the illustrated elements, processes and devices.

Figure 3:
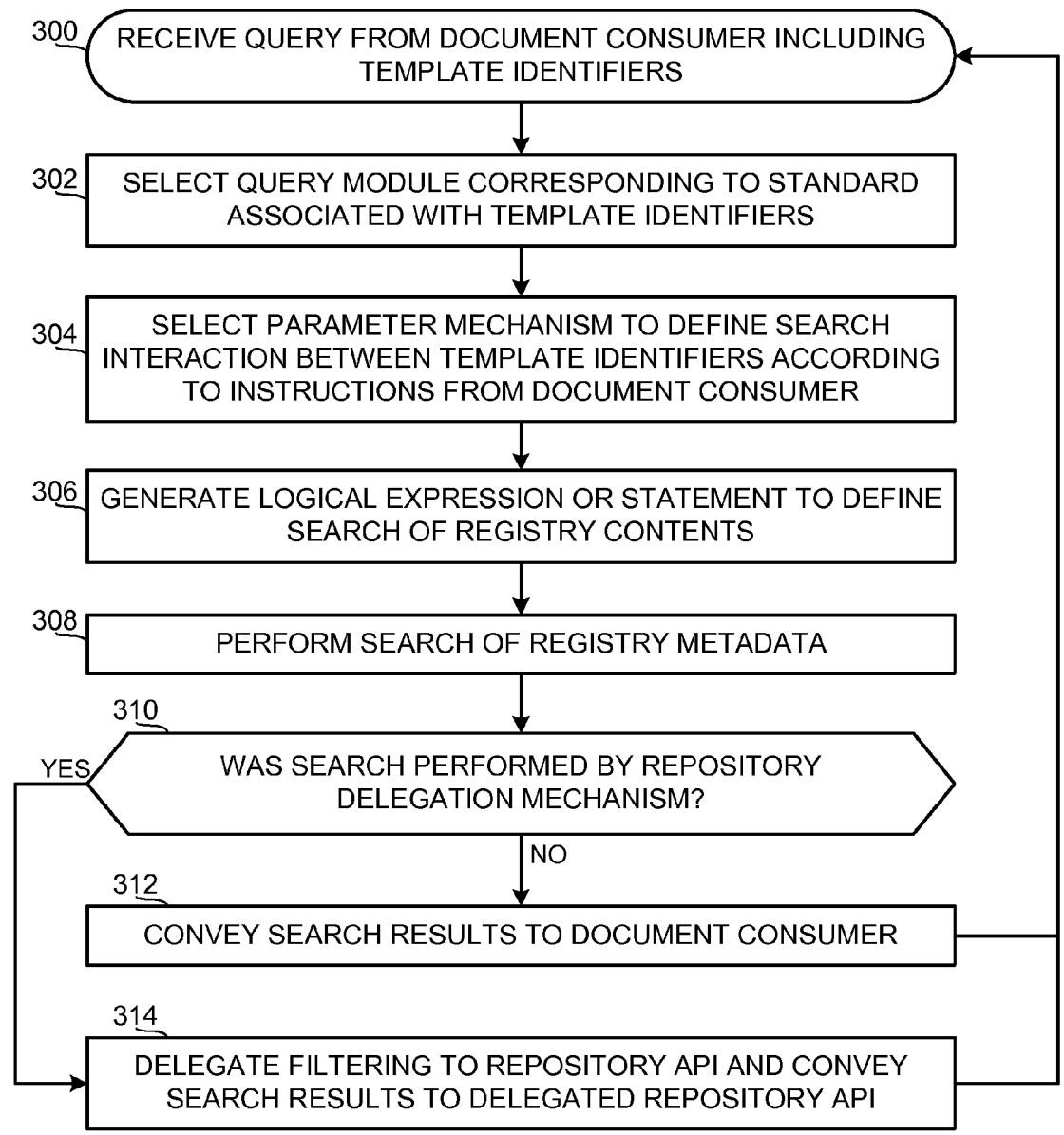
FIG. 3 is a flow diagram representative of example machine readable instructions that may be executed to implement the example query module of FIGS. 1 and/or 2.
Figure 4:
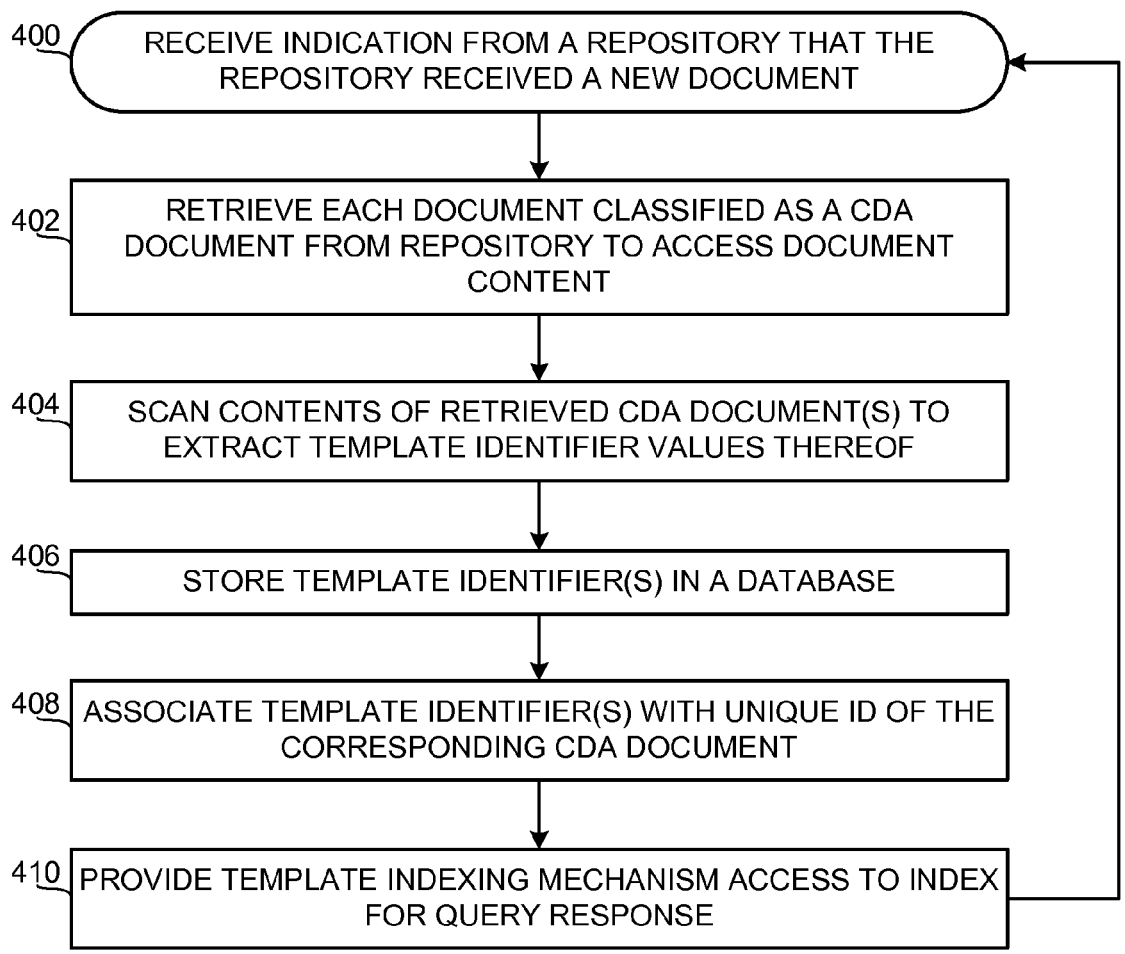
FIG. 4 is a flow diagram representative of example machine readable instructions that may be executed to implement the example template indexing mechanism of FIG. 2.

FIGS. 3 and 4 depict example flow diagrams representative of processes that may be implemented using, for example, computer readable instructions that may be used to implement the example query manager 120 of FIGS. 1 and/or 2 and/or to implement the example template indexer 218 of FIG. 2, respectively. The example processes of FIGS. 3 and 4 may be performed using a processor, a controller and/or any other suitable processing device. For example, the example processes of FIGS. 3 and 4 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIGS. 3 and 4 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 3 and 4 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 3 and 4 may be implemented manually or as any combination(s) of any of the foregoing techniques, for example, any combination of firmware, software, discrete logic and/or hardware. Further, although the example processes of FIGS. 3 and 4 are described with reference to the flow diagrams of FIGS. 3 and 4, other methods of implementing the processes of FIGS. 3 and 4 may be employed. For example, the order of execution of the blocks may be changed, and/or some of the blocks described may be changed, eliminated, sub-divided, or combined. Additionally, any or all of the example processes of FIGS. 3 and 4 may be performed sequentially and/or in parallel by, for example, separate processing threads, processors, devices, discrete logic, circuits, etc.

FIG. 3 is a flow diagram representative of example machine readable instructions that may be executed to implement the example query manager 120 of FIGS. 1 and/or 2. In the illustrated example of FIG. 3, the query manager 120 of the registry 104 receives, at the communication interface 200, a query from the document consumer 118 that includes template identifiers (block 300). As described above, template identifiers provide information regarding the content and/or the type(s) of content included in a document conforming to a certain standard.

For purposes of illustration, the document consumer 118 may be a researcher that desires information related to a certain type of patient and/or medical situation. For example, the researching document consumer 118 may be researching heart arrhythmias. To initially limit his or her search using known query options, the researcher 118 includes the term 'heart arrhythmia.' However, as described above, previous query services are limited. Using the example query manager 120 described herein, the researcher 118 can enhance his or her query by adding the template identifiers received at block 300 to the query. As an example, the researcher 118 may include a first template identifier that confirms that corresponding documents include active medication lists for the patient associated with each document. By including such a template identifier in the query, the researcher 118 knows that returned results will be filtered to include only those healthcare documents that conform to the standard defined by the template identifier. In other words, the example query module 120 provides the researcher 118 with documents that include active medications lists in accordance with the template identifier included in the query in addition or in lieu of traditional query terms.

The example communication interface 200 of FIG. 2 can recognize that the query includes template identifiers and, in response, determines which standard the received template identifiers are associated with. Based on the standard associated with the received template identifiers, the communication interface 200 selects one of the query modules 202*a*-*x* to handle the received query (block 302). In the illustrated example of FIG. 3, the received template identifiers are associated with the HL7 CDA. That is, the template identifiers will provide information regarding to which of a plurality of CDA standards the document conforms. Thus, the example communication interface 200 selects the CDA template identifier query module 202*a* to handle the received query.

As described above, the document consumer 118 is also capable of providing instructions to the query manager 120 regarding a search interaction between the template identifiers. The example communication interface 200 of FIG. 2 and the CDA template identifier query module 202*a* is capable of identifying the search interaction specified in the query. Using the type of identified type of search interaction, the example communication interface 200 or the CDA template identifier query module 202*a* selects one of the parameter mechanisms 204 to handle the received query (block 304). In the illustrated example, the query sent by the document consumer 118 includes multiple lists of template identifiers. Furthermore, information sent with the query indicates that the document consumer 118 desires healthcare documents that include any of the template identifiers specified in each of the received lists of template identifiers. Thus, in the illustrated example, the multi-list parameter mechanism 214 is selected to handle the received query.

As described above in connection with FIG. 2, the example multi-list parameter mechanism 214 generates a logical statement or expression to define a search of the registry contents (block 306). The logical statement or expression generated by the multi-list parameter mechanism 214, which includes the metadata corresponding to the template identifiers, defines constraint(s) to be used in the search of the content of the registry 104 metadata. In the illustrated example, the constraint(s) are defined by logical operators arranged to find documents that include any of the template identifiers specified in each of the received lists of template identifiers (e.g., as described above in connection with FIG. 2).

A selected one of the content matchers 206 receives an output from the selected one of the parameter mechanisms 204, which is the multi-list parameter mechanism 214 in the illustrated example. To select one of the content matchers 206, the CDA query module 202*a* may receive instructions reflecting a desired search method from the document consumer 118. Alternatively, the CDA query module 202*a* may have a default setting to select one of the content matchers 206 (e.g., the template indexing mechanism) in the absence of instructions to the contrary. In some examples, the template indexer 218 may index received metadata related to template identifiers regardless of whether the template indexing mechanism 216 is selected to perform the search of the registry 104 for a particular query. That is, the template indexer 218 may be configured to analyze and index each template identifier received by the CDA query module 202*a* and/or, more generally, the query manager 120.

In the illustrated example, the template indexing mechanism 216 is selected from the content matchers 206. Using the logical expression including the template identifiers generated by the multi-list parameter mechanism 214, the example template indexing mechanism 216 searches the metadata of the registry 104 to identify documents matching the criteria of the logical expression (block 308). As described above, the example template indexing mechanism 216 utilizes the template indexer 218 to perform the search. Any matching documents are stored as the search results 208.

In some examples, the repository delegation mechanism 220 is selected to perform the search of the registry 104. When the CDA query module 202 determines that the search was not performed by the repository delegation mechanism 220 (block 310), such as when the template indexing mechanism 216 is selected as described above, the search results 208 are conveyed to the document consumer 118 via any suitable method or device (block 312).

Otherwise, when the repository delegation mechanism 220 performed the search of the registry 104 (block 310), the example repository delegation mechanism 220 delegates filtering of search results to one or more of the repositories 110a-d (block 314). As described above, the repositories 110a-d include application program interface(s) (API(s)) dedicated to filtering search results including documents. For example, the search results may be filtered using logical expression(s) similar to those generated by the parameter mechanisms 204.

FIG. 4 is a flow diagram representative of example machine readable instructions that may be executed to implement the example template indexing mechanism 216 of FIG. 2. As described above, the repositories 110a-d of the example healthcare data system 100 of FIG. 1 receive and store healthcare documents for sharing across an affinity domain. In the illustrated example of FIGS. 2 and 4, the repositories 110a-d are configured to inform the example template indexing mechanism 216 of receipt of a new healthcare document. Thus, the template indexing mechanism 216 receives indications from the repositories 110a-d (block 400). In response, the template indexing mechanism 216 retrieves each new document classified as a CDA document from the one of the repositories 110a-d that conveyed the indication of new documents. In the illustrated example, the template indexing mechanism 216 received the indication from the first repository 110a. For example, the temple indexing mechanism 216 may determine which of the newly entered documents of the repository 110a has a MIME (Multipurpose Internet Mail Extensions) type and Format Code that classifies document content as an HL7 CDA document.

When the temple indexing mechanism 216 retrieves the new CDA documents, the temple indexing mechanism 216 scans the content of the CDA documents to extract template identifier values included therein (block 404). For example, the temple indexing mechanism 216 may identify matches of an Xpath expression (e.g., //templateID@root) associated with a document. The extracted template identifier(s) are then stored in a database and/or any suitable storage device or structure (block 406).

To index the identified and stored template identifier(s), the example template indexer 218 associates each of the stored template identifier(s) with a unique ID associated with the CDA document (block 408). The information generated by the template indexer 218 (i.e., the index described herein) facilitates searching of the registry 104 by providing the associations of the unique IDs and the template identifier(s) corresponding to the documents of the repositories 110a-d. The temple indexing mechanism 216 then gains access to the index such that the temple indexing mechanism 216 can perform the search(es) described herein (block 410).

Figure 5:
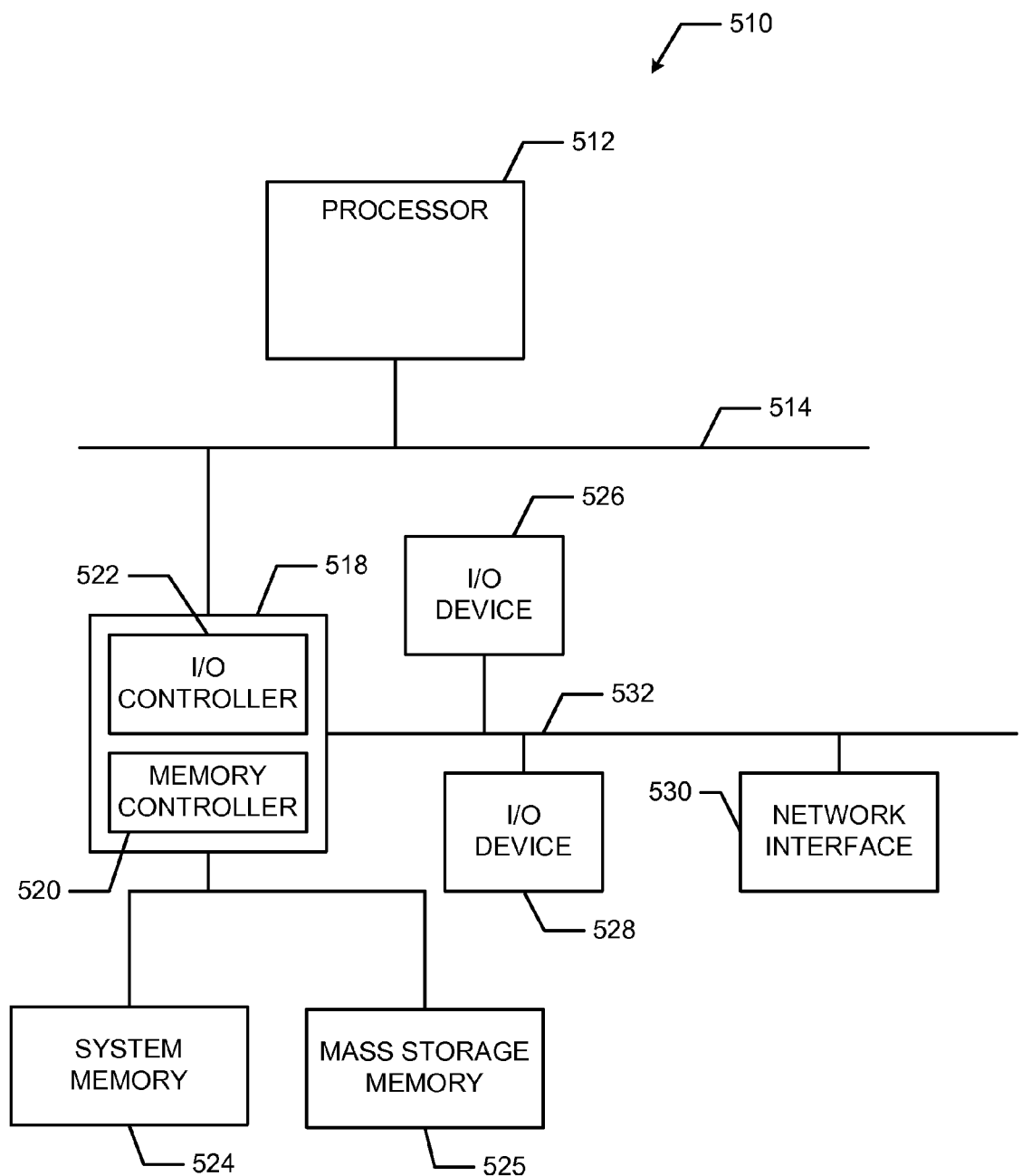
FIG. 5 is a block diagram of an example processor system that may be used to execute the machine readable instructions of FIG. 3 to implement the example query module of FIGS. 1 and/or 2, and/or that may be used execute the machine readable instructions of FIG. 4 to implement the example template indexing mechanism of FIG. 2.

FIG. 5 is a block diagram of an example processor system 510 that may be used to implement the apparatus and methods described herein. As shown in FIG. 5, the processor system 510 includes a processor 512 that is coupled to an interconnection bus 514. The processor 512 may be any suitable processor, processing unit or microprocessor. Although not shown in FIG. 5, the system 510 may be a multi-processor system and, thus, may include one or more additional processors that are identical or similar to the processor 512 and that are communicatively coupled to the interconnection bus 514.

The processor 512 of FIG. 5 is coupled to a chipset 518, which includes a memory controller 520 and an input/output (I/O) controller 522. As is well known, a chipset typically provides I/O and memory management functions as well as a plurality of general purpose and/or special purpose registers, timers, etc. that are accessible or used by one or more processors coupled to the chipset 518. The memory controller 520 performs functions that enable the processor 512 (or processors if there are multiple processors) to access a system memory 524 and a mass storage memory 525.

The system memory 524 may include any desired type of volatile and/or non-volatile memory such as, for example, static random access memory (SRAM), dynamic random access memory (DRAM), flash memory, read-only memory (ROM), etc. The mass storage memory 525 may include any desired type of mass storage device including hard disk drives, optical drives, tape storage devices, etc.

The I/O controller 522 performs functions that enable the processor 512 to communicate with peripheral input/output (I/O) devices 526 and 528 and a network interface 530 via an I/O bus 532. The I/O devices 526 and 528 may be any desired type of I/O device such as, for example, a keyboard, a video display or monitor, a mouse, etc. The network interface 530 may be, for example, an Ethernet device, an asynchronous transfer mode (ATM) device, an 802.11 device, a DSL modem, a cable modem, a cellular modem, etc. that enables the processor system 510 to communicate with another processor system.

While the memory controller 520 and the I/O controller 522 are depicted in FIG. 5 as separate blocks within the chipset 518, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A computer-implemented method of providing a query service, comprising:
    enabling a user to submit a query including a template identifier selected from a plurality of available template identifiers, the respective template identifiers indicative of conformance with a standard;
    identifying, via a processor, the template identifier of the query and using the identified template identifier to select a query module dedicated to a first standard corresponding to the identified template identifier; and
    generating, using the processor, an expression including data associated with the first standard to which the selected query module is dedicated to define a search corresponding to the query received from the user, wherein the expression is used to search a data collection to identify documents having metadata associated with the selected template identifier.

2. A method as defined in claim 1, further comprising selecting one of a plurality of parameter mechanisms associated with the selected query module to generate the expression based on logical instructions received with the template identifier.

3. A method as defined in claim 1, further comprising, in response to receiving an indication from a repository that the repository received a new document, determining whether the new document in the repository is classified as a document of a second standard.

4. A method as defined in claim 3, further comprising extracting template identifier information from the new document when the new document is classified as a document of the second standard.

5. A method as defined in claim 1, wherein generating the expression includes arranging a logical operator with a second selected template identifier according to a desired logical relationship between the template identifiers.

6. A method as defined in claim 5, wherein the logical relationship is defined by the user.

7. A method as defined in claim 1, wherein the template identifier is associated with a Clinical Document Architecture standard.

8. A tangible computer readable medium having instructions stored thereon that, when executed, cause a machine to at least:
    enable a user to submit a query including a template identifier selected from a plurality of available template identifiers, the respective template identifiers indicative of conformance with a standard;
    identify the template identifier of the query and use the identified template identifier to select a query module dedicated to a first standard corresponding to the identified template identifier; and
    generate an expression including data associated with the first standard to which the selected query module is dedicated to define a search corresponding to the query received from the user, wherein the expression is used to search a data collection to identify documents having metadata associated with the selected template identifier.

9. A tangible computer readable medium as defined in claim 8, wherein the instructions cause the machine to select one of a plurality of parameter mechanisms associated with the selected query module to generate the expression based on logical instructions received with the template identifier.

10. A tangible computer readable medium as defined in claim 8, wherein the instructions cause the machine to, in response to receiving an indication from a repository that the repository received a new document, determine whether the new document in the repository is classified as a document of a second standard.

11. A tangible computer readable medium as defined in claim 10, wherein the instructions cause the machine to extract template identifier information from the new document when the new document is classified as a document of the second standard.

12. A tangible computer readable medium as defined in claim 8, wherein generating the expression includes arranging a logical operator with a second selected template identifier according to a desired logical relationship between the template identifiers.

13. A tangible computer readable medium as defined in claim 12, wherein the logical relationship is defined by the user.

14. A tangible computer readable medium as defined in claim 8, wherein the template identifier is associated with a Clinical Document Architecture standard.

15. An apparatus to provide a query service, comprising:
    a first query module assigned to handling queries of a first one of a plurality of standards related to content of a document;

a second query module assigned to handling queries of a second one of the standards different than the first standard;

a communication interface to:
- identify which of a plurality of template identifiers was selected by a user in connection with a received query, the template identifiers respectively indicative of conformance with one of the plurality of standards;
- when the user selected a first one of the template identifiers indicative of conformance with the first standard, assign the received query to the first query module; and
- when the user selected a second one of the template identifiers indicative of conformance with the second standard, assign the received query to the second query module; and a generator to generate an expression for the query, wherein the expression is used to search a data collection to identify documents having metadata associated with a selected one of the template identifiers, wherein at least one of the first query module, the second query module, the communication interface, or the generator is implemented via a logic circuit.

16. An apparatus as defined in claim 15, further comprising a content matcher to perform the search of the data collection according to the expression.

17. An apparatus as defined in claim 15, wherein the generator is to generate the expression to include a logical operator according to a desired logical relationship.

18. An apparatus as defined in claim 17, wherein the logical relationship is selected by the user.

19. An apparatus as defined in claim 15, wherein the generator comprises a plurality of parameter mechanisms, and one of the parameter mechanisms is selected to generate the expression.

20. An apparatus as defined in claim 15, further comprising a template indexer to, in response to receiving an indication from a repository that the repository received a new document of a second standard, generate an index using template identifier information extracted from the new document.

* * * * *